United States Patent [19]

Kuzma

[11] Patent Number: 5,272,283
[45] Date of Patent: Dec. 21, 1993

[54] FEEDTHROUGH ASSEMBLY FOR COCHLEAR PROSTHETIC PACKAGE

[75] Inventor: Janusz Kuzma, Stanmore, Australia

[73] Assignee: Commonwealth of Australia, Canberra, Australia

[21] Appl. No.: 701,660

[22] Filed: May 16, 1991

Related U.S. Application Data

[60] Division of Ser. No. 350,574, May 11, 1989, Pat. No. 5,046,242, which is a continuation of Ser. No. 402,227, Jul. 27, 1982, abandoned.

[51] Int. Cl.$^5$ .............................................. H05K 1/00
[52] U.S. Cl. ................... 174/262; 174/50.61; 174/255
[58] Field of Search ............... 174/255, 256, 258, 262, 174/264, 266, 50.60, 50.61; 29/624, 626

[56] References Cited

U.S. PATENT DOCUMENTS

| | | | |
|---|---|---|---|
| 3,517,437 | 6/1970 | Szobonya | 29/624 |
| 3,545,606 | 12/1970 | Bennett | 29/626 |
| 3,582,978 | 6/1971 | Petersen | 174/50.61 X |
| 3,665,239 | 5/1972 | Morinaud | 174/50.61 X |

Primary Examiner—Leo P. Picard
Assistant Examiner—Trinidad Korka
Attorney, Agent, or Firm—Gottlieb, Rackman & Reisman

[57] ABSTRACT

A cochlear prosthetic package having a cup-shaped titanium case with a ceramic plate; a plurality of hermetically-sealed feedthroughs are formed in the plate by sintering the plate with hollow metallic tubes located in plate holes and then sealing at least one end of each tube. An electrode cable connector is provided which allows removal and replacement of a case even in the presence of body fluids. A telemetry coil is contained in a metallic tube which extends out of the case; the coil-containing tube has its two ends hermetically-sealed to the case by ceramic insulating bushings.

8 Claims, 3 Drawing Sheets

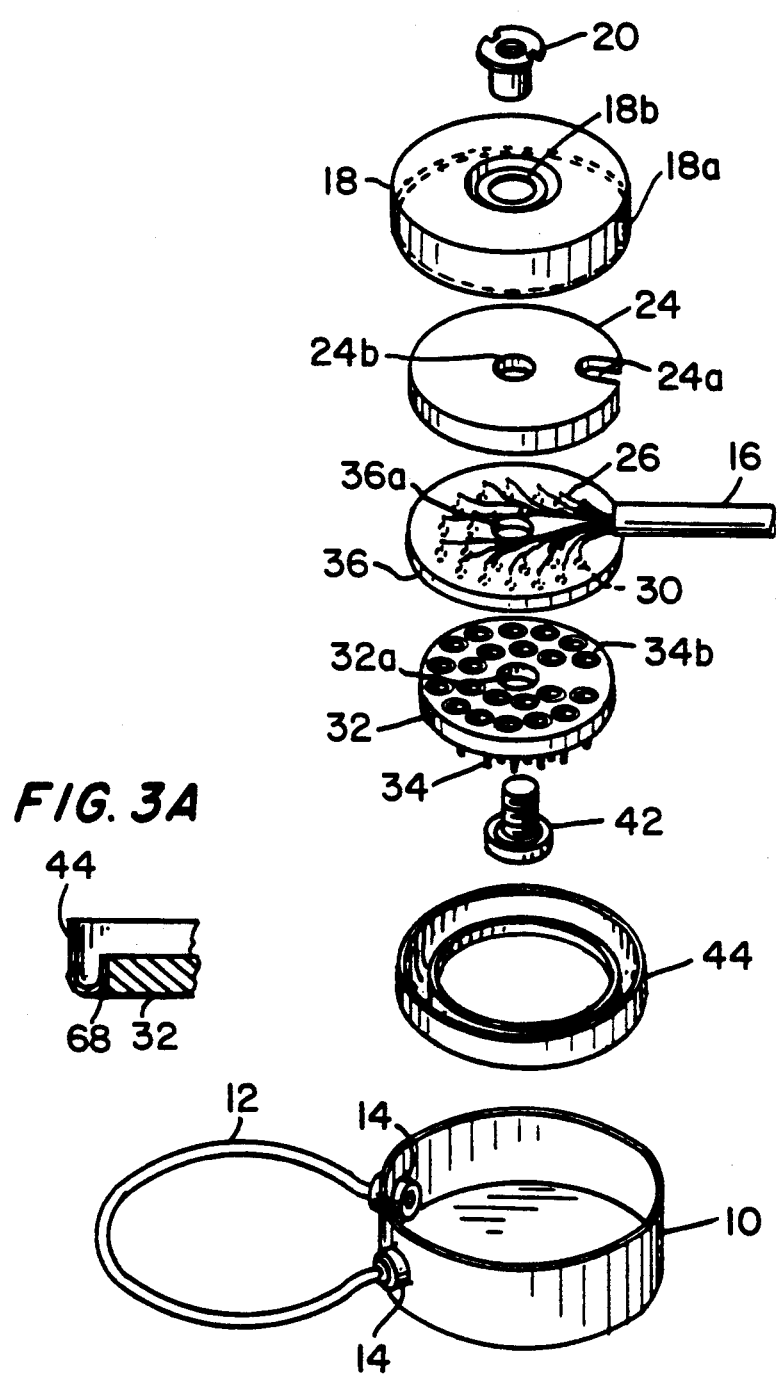

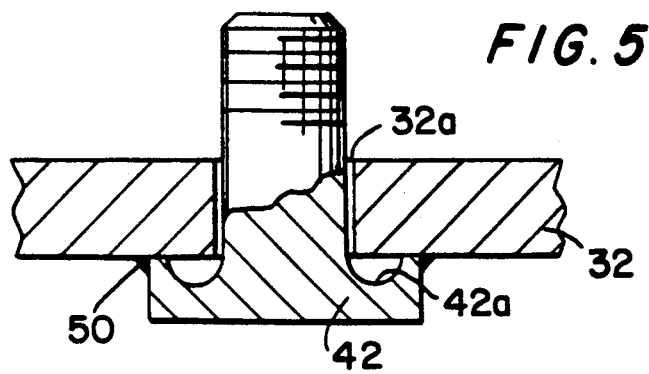
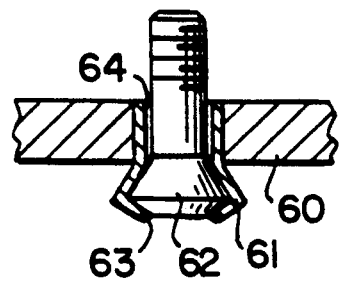
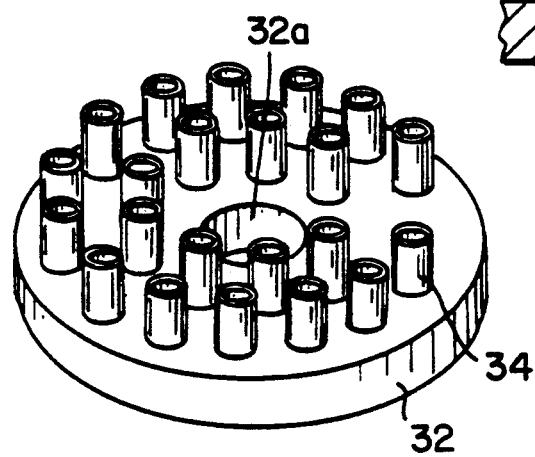
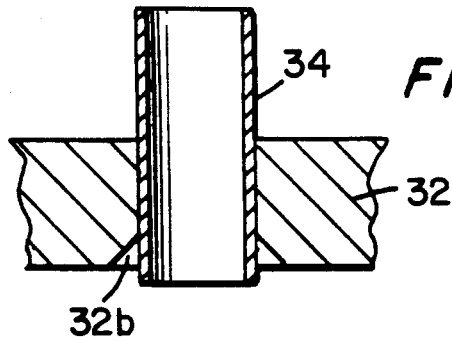
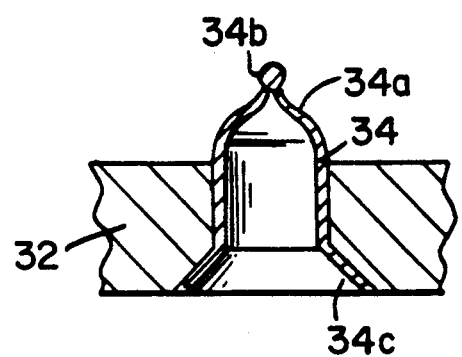

FEEDTHROUGH ASSEMBLY FOR COCHLEAR PROSTHETIC PACKAGE

This application is a division of application Ser. No. 350,574 filed May 11, 1989, now U.S. Pat. No. 5,046,242 issued Sep. 10, 1991, which in turn is a continuation of application Ser. No. 402,227 filed Jul. 27, 1982 and now abandoned.

This invention relates to implantable medical electronic devices such as pacemakers and cochlear prostheses, and more particularly to a cochlear prosthesis which must be hermetically sealed and have a telemetry capability.

Implantable medical prostheses of many different types are now in common use throughout the world. These devices, such as pacemakers and bone growth stimulators, not only provide electrical stimulation but also often interact in two-way telemetry systems. Operation of a prosthesis can be controlled by an externally transmitted signal, and the prosthesis itself can generate and transmit to the outside world a signal indicative of its operation or patient condition. There is a great degree of cross-fertilization in the sense that techniques developed for one particular type of prosthesis are often eventually used in connection with others. A good example of this are the techniques of hermetic sealing, originally developed for pacemakers but now used for medical prosthesis in general.

Depending on the particular prosthetic device which is involved, the solution of one problem may be more vexing than the solutions of others. But there is one type of device, a cochlear prosthesis, for which a confluence of design criteria (some of which are competing) has severely limited progress.

In its usual form, a cochlear prosthesis "system" consists of two parts. The first is an "electronics" package which is implanted in the mastoid bone behind the ear; a connector assembly, having perhaps 22 individual electrodes extended to a cochlea, is removably attached to the package. The second part of the system consists of an external transmitter/receiver. The external unit not only functions in a telemetry capacity, but also serves to transfer power to the implanted unit.

The cochlear prosthetic package must be constructed in such a way that only bio-compatible materials are in contact with body tissues, a design criterion common to implantable prosthetic devices in general. Similarly, the entire package should be hermetically sealed to prevent the ingress of body fluids which could have a damaging effect on the electronic circuits in the package, and to prevent potentially harmful substances which may be inside the package from contacting body fluids. Long life is assured by hermetic sealing, and it is known that a pacemaker, for example, can operate for many years before a replacement is necessary, e.g., because of battery depletion.

The problem with a cochlear prosthesis is that entire replacement of the device is probably not feasible. The electrode assembly, once it has been in place in a cochlea for several years, probably cannot be explanted without damaging the cochlea itself. Thus the electrode assembly itself must have a long life, e.g., fifty years. The package containing the electronic circuits can be designed for long life, e.g., as in pacemaker technology. However, in the unlikely event of a failure, it is more likely to be in the electronics package than the electrode assembly. In addition, projected advances in technology will make it desirable to be able to replace the electronics package with a more sophisticated unit. Thus it is necessary to be able to disconnect the electronics package from the electrode assembly to enable replacement with another package, and a connector arrangement is required. Permanent, hermetic connections (such as conventionally used in pacemakers) are unsuitable because disconnection and re-connection are not possible.

The connector problem is much more severe in the case of a cochlear prosthesis than it is in the case of a pacemaker. A typical pacemaker requires at most four electrodes to be connected to the internal electronics via hermetically sealed electrical feedthroughs. The pacemaker feedthroughs are much more widely separated than are those of a cochlear prosthesis primarily because of the large number of feedthroughs in the latter, typically 10–22 in number. Each of the many connections between the hermetically-sealed electronics package and an individual electrode in the electrode assembly must have low electrical resistance. Conversely, it has been found important that the resistances between contacts be maintained as high as possible for long-term proper operation of the device. What further complicates matters is that not only must the connector be capable of attaching the electrode assembly to the electronics package several times without degrading the performance, but each re-assembly must take place in an environment where fluid ingress cannot be prevented; since the electrode assembly is permanently implanted, every attachment of a new package to the electrode assembly must take place in the patient's head.

It will be apparent to those skilled in the art that this type of "connector" problem is not limited to implantable medical prostheses. There are many fields of electronics where it is necessary to make a similar high quality but difficult connection, such as in high pressure, high temperature, marine or chemically reactive environments. As will become apparent below, the connector aspects of the present invention are equally applicable to such other electronic systems, as is the technique for making feedthroughs which will now be described.

The second major problem in the design and construction of a cochlear prosthetic package relates to the feedthroughs. The most pertinent prior art in this regard consists of techniques for making feedthroughs in pacemakers. A pacemaker is typically contained in a biocompatible titanium case. In order to connect the electronics inside the package to the electrodes, it is necessary to extend through the case up to four conducting pins. This is usually accomplished by providing ceramic feedthroughs. For each pin, a hole is provided in the titanium case and a ceramic bushing is placed in the hole. A conducting pin is extended through a hole in the ceramic bushing to connect an external electrode to the electronic circuit inside the case. An hermetic seal is established by utilizing brazing techniques—both at the case/ceramic interface and the ceramic/pin interface. The ceramic bushings are not only bio-compatible, but they also serve as insulators.

For a pacemaker, it is anticipated that more and more feedthroughs will be required as the years go by. While most prior art pacemakers utilize only one or two feedthroughs, with the advent of dual chamber pacemakers it is apparent that four feedthroughs are desirable. Furthermore, as miniaturization techniques improve, it is expected that pacemakers will include many more sensing functions than they now have, and this will in turn require additional feedthroughs for connecting the electronic circuits to sensor leads. But it is presently in the case of a cochlear prosthesis that the problems in fabricating the feedthroughs are most severe. In the illustrative embodiment of the invention, 22 feedthroughs are required. It is extremely time-consuming and costly to provide such feedthroughs using prior art techniques. If prior art techniques are used, not only must 22 individual feedthroughs be assembled, but a brazing operation at 22 sites is required—all in a very confined space. Because of the large number of hermetic brazes required to be performed at once, I have discovered that the brazing technique results in low yields, leading to prohibitive manufacturing costs. It is clear that if the costs of making cochlear prostheses (and future pacemakers) are not to get out of hand, a different approach must be taken for implementing feedthroughs.

Still another general problem relates to packaging of telemetry systems. The present invention does not concern itself with the electronic aspects of an implantable medical prosthesis, but rather with packaging of the telemetry coil. (Telemetry systems which are particularly advantageous for use in an implantable cochlear prosthesis are disclosed in Daly-Money applications Ser. Nos. 252,319 and 252,313, both filed on Apr. 9, 1981, now respectively U.S. Pat. Nos. 4,408,608 and 4,533,988, and entitled respectively "Implantable Tissue-Stimulating Prosthesis" and "On-Chip CMOS Bridge Circuit", both of which applications are hereby incorporated by reference.) The package must be designed in such a way that efficient transfer of power and information between the external and internal coils is possible. The single coil in the implanted package may be used for either transmitting or receiving of information, or both, as well as for receiving power from the external part of the system.

There are two standard prior art coil packaging designs. The first is to include one or more coils inside the same package which contains the electronic circuits. This approach requires the package to be made of a nonconducting material (i.e., not metal) to allow the efficient transfer of power and data at useful frequencies. Achieving an hermetic seal in such a case is difficult. Even if the package is non-metallic, but uses a metallic band to provide the hermetic sealing (e.g., involving conventional brazing materials such as are used in the semiconductor industry to provide hermetic sealing of integrated circuit packages), the seal itself will act as a short-circuited turn of wire and will degrade the efficiency of power and information transfer. (Conventional brazing materials for joining metallic to ceramic components, e.g., in the semiconductor industry, are often gold based, or use some other metal, and have unproven biocompatibility. Brazing materials such as commonly used in pacemakers for joining ceramic to titanium are acceptable.) The use of a metallic lid, even if it is on the side of the package facing away from the incoming radiation, also has a degrading effect on the transmission efficiency. An even greater shortcoming of the coil-inside-the-package approach is that an obvious constraint is placed on the size of the coil; in general, larger coils will allow more efficient power and information transfer, but the package size is limited by implant requirements.

The second prior art approach involves using an external coil which is connected to the electronic circuits inside the hermetically-sealed package via a pair of feedthroughs. There are two problems with this approach. The first is that it is not possible to hermetically isolate the wire from the surrounding body fluids. While epoxy or Silastic material may be placed around the coil, such coatings do not provide an hermetic seal and the ingress of body fluids can give rise to short useful life. The second problems relates to the large voltages which may be generated. Typically, potential differences in the order of a volt may be induced across the two ends of each individual turn in the coil. If there are 15 turns, as there are in the illustrative embodiment of the invention, a large voltage signal may be induced across the two ends of the coil as a result of the incoming signal from the outside world. Such a large potential across the feedthrough pins may lead to corrosion, and may be biologically harmful.

It is a general object of this invention to provide feedthrough assembly for a prosthetic package including cochlear prosthesis or other implantable medical electronic device which overcomes the aforesaid problems.

Briefly, in accordance with the principles of the invention, the feedthroughs are made using an approach which is totally different from those of the prior art. A plate or carrier of unfired or "green" ceramic is formed with 22 small holes arranged around a larger central hole. Twenty 2-ended platinum tubes are placed axially into the smaller holes. Each tube has an outside diameter approximately the same as the respective hole so that a snug fit is obtained. The length of the tube is about twice the thickness of the ceramic plate. I have discovered that a wall thickness of about one tenth the outside diameter of the platinum tube gives good results. The platinum is 99.9% pure, or better. The tubes are placed on a flat, high alumina ceramic sheet so that one end of the tubes is flush with one surface of the green ceramic plate.

The assembly is then placed in a furnace and the green ceramic is sintered or fired in the usual way. As the ceramic sinters, it shrinks, typically in the order of 10–15% in all dimensions. The process of shrinking causes pressure to be exerted around the platinum tubes, such that a platinum-to-ceramic reaction bond is formed between the tube and the ceramic along the length of the tube in the ceramic, and around the entire circumference. The bond so formed results in an hermetic seal between the platinum and the ceramic.

The physical properties of the materials are important. First, a ceramic should be used such that the firing temperature is about 0.9 times the melting point of platinum (i.e., about 1500 degrees C.). Other metals and ceramics may be used, but this temperature ratio is important. Second, the platinum is a ductile material, and furthermore the process of heating and slow cooling anneals the platinum. Thus, in the cooling of the assembly, as the whole assembly shrinks further, the bond between the platinum and ceramic is not broken by the platinum shrinking away from the ceramic as a result of different coefficients of thermal expansion, because the platinum is able to deform. Third, at the sintering temperature of the ceramic, the platinum material becomes partly plastic, and does not crack around the platinum tubes.

This technique is quite different from conventional platinum-to-ceramic reaction bonding techniques in several important ways. Conventional bonding is usually between flat pieces of ceramic and platinum foil or sheet. I have developed this technique for a circular bond. In addition, it is extremely difficult to make a large number of platinum-to-ceramic bonds simultaneously using the conventional technique of externally applied pressure. Particularly important in this invention is the fact that independent pressure is produced in each hole around each platinum part, and there is thus no theoretical limit to the number of simultaneous bonds possible; also, the dimensions may be extremely small or quite large with good results. The prior art technique is often used to join two pieces of ceramic together, and in order to make a single sided bond, another refractory material is required to apply the pressure to the platinum. This is often graphite, but the use of graphite requires either a vacuum furnace or an inert atmosphere (e.g., argon) to prevent the graphite from burning at the higher temperatures involved.

Following sintering, at least one end of the tube is closed off, e.g., by welding, to complete the hermetic seal. Alternatively, pre-formed platinum parts with an end or ends already closed off may be used. It is important only that the portion of the platinum part in the ceramic is not solid in cross section.

Despite the simplicity of the technique, it has been found that consistent perfect hermetic seals are achieved. (Thus far, the technique has been found to work only if feedthrough tubes, or tubular pre-formed parts, are used, rather than solid rods.) The net result is that a plurality of feedthroughs may be formed with a minimum of effort since very little individual feedthrough processing is required. A completely hermetically sealed package may be obtained simply by brazing the circumferential edge of the ceramic plate to an opening in an otherwise completely closed titanium case. Instead of requiring an individual braze on each feedthrough, all that is required is a single brazing of the ceramic plate to the case. Close feedthrough spacings can be achieved because the only "work" required on each feedthrough is the closing of at least one end of the respective tube. Even this can be eliminated by the use of pre-formed parts.

There remains the problem of connecting the electrode assembly to the case in a manner which assures the electrical characteristics described above, as well as allowing occasional replacement of the case. In the illustrative embodiment of the invention, it is only the end of each tube inside the case which is sealed. The open end of each of feedthrough, which extends away from the hermetically sealed case, is formed to have a concavity. The connector itself consists of a series of platinum wires (connected to the individual electrodes in the electrode assembly), each of which terminates at an end shaped to mate with a respective formed feedthrough concavity. The wire contacts themselves are embedded in a Silastic sheet (type 4120). This sheet is backed by a titanium cover, with another Silastic sheet (also type 4210) being interposed between the cover and the Silastic sheet which contains the wire contacts. A single screw extends up from the ceramic plate. (The screw has a special configuration, as will be described below.) This screw passes through the two Silastic sheets and the titanium cover, and is secured by a nut. The force holding the connector together is provided by a single centrally-located screw, but the force is distributed over the connector surface by the elastic properties of the Silastic sheets, especially the sheet disposed against the cover. As will become apparent below, if the exposed surface of the ceramic plate is highly polished to a mirror finish, and the cover is held on with sufficient pressure, fluid is excluded in the connector which could form a conducting path between contacts.

As for the coil, the advantages of both the internal and external approaches are achieved, without the disadvantages of either. The coil is contained inside a metallic tube made of bio-compatible material. The preferred material is platinum, although titanium or stainless steel may be suitable. The tube is attached via a pair of insulating ceramic bushings which are brazed to the titanium package. (The tube ends are secured in the bushings, with an hermetic seal, in a manner comparable to the way the feedthroughs are made.) The metallic tube is thus topologically continuous with the inside of the package. Because the ends of the tube are not electrically connected together (other than through the tube), the tube does not form a shorted turn which otherwise would make impossible the performance of the data and power link. There is no metal inside the coil, other than the tube which contains the coil, which would otherwise similarly degrade the data and power link efficiency. The coil size is not limited by the package, the tube can be bent to any desired shape, and a complete hermetic seal is achieved.

Further objects, features and advantages of the invention will become apparent upon consideration of the following detailed description in conjunction with the drawing, in which:

FIG. 3 is an exploded perspective view showing the several component parts of the package of FIG. 1;

FIG. 3A is a sectional view showing how ceramic plate 32 is secured to lid 44;

FIG. 5A is a detailed view illustrating the shape of the screw which extends through the connector, and FIG. 5B is an alternative embodiment of the screw; and FIGS. 6A, 6B and 6C illustrate the manner in which the feedthroughs are fabricated, with FIG. 6A depicting the start of the feedthrough fabrication, and FIGS. 6B and 6C showing successive steps performed on an individual feedthrough in the overall method.

Figure 1:
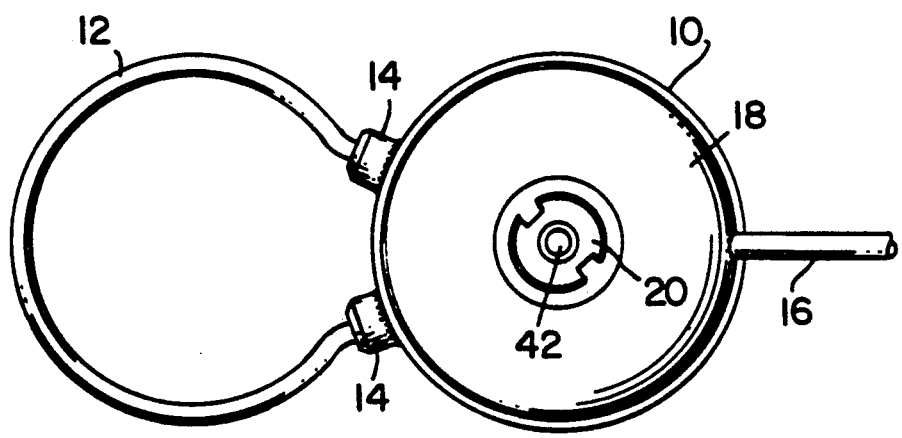
FIG. 1 is a top view of the package of the illustrative embodiment of the invention (with the details of the electrode assembly being omitted since such assemblies are well known in the art)
Figure 2:
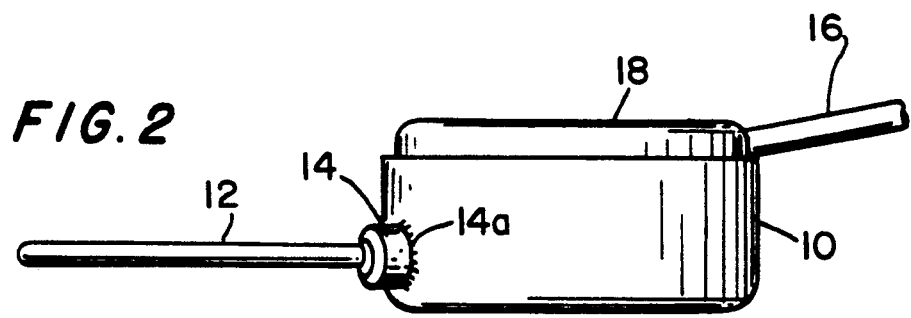
FIG. 2 is a side view of the package of FIG. 1.

The package illustrated in FIGS. 1 and 2 includes a titanium case 10, and a titanium connector cover 18. The cover is coupled to the case by a titanium screw 42 and a titanium nut 20. Cable 16, extended to the electrode assembly (not shown), exits the cover 18 as shown. A pair of ceramic insulating bushings 14 are brazed to the titanium case, as shown at 14a, in a conventional manner.

Platinum tube 12 has two ends inserted into the holes which extend through the ceramic bushings, and the ends of the tube are hermetically sealed to the bushings as will be described below. An important feature of the design is that the two ends of the tube are not electrically connected so that the tube does not comprise a shorted turn which would otherwise absorb radiated power. In the illustrative embodiment of the invention, the coil (not shown) comprises 15 turns, each turn passing through the tube and the inside of the case from one bushing to the other. The two ends of the 15-turn coil are connected to the electronic circuits (not shown) inside the case.

An alternative embodiment which has been found to be useful is to use a single-turn coil which is coupled into a small transformer wound on a ferrite toroid, where the number of turns on the secondary may be adjusted to give the required voltage, and may be optimized for best transfer efficiency. In one embodiment, the single-turn coil can be a single turn of insulated copper wire contained within the platinum tube. Alternatively, multistranded platinum wire may be welded to the platinum tube coming through the ceramic feedthroughs brazed into the titanium case. That is, instead of the tube being continuous from one ceramic bushing to the other, only short pieces of tube are used, and solid or stranded wire is hermetically welded to the tubes to complete the coil. This technique has the advantages that the whole assembly is more robust, since the receiving coil is solid wire, and can be easily bent (as opposed to a tube which is subject to kinking and fracture on bending). In addition, there are some advantages to be gained in the electrical performance by using a single-turn receiver coil.

As mentioned above, the details of the electronic circuits are not important for an understanding of the present invention. The entire assembly may be encased in Silastic (not shown), to insure that no sharp edges are exposed, and to cushion and protect the package once it is implanted in the body. To remove the case from the connector the Silastic can be cut. When a new case is then attached to the connector, the new case can be encased in Silastic before reimplantation. The only difference between the Silastic coatings around the overall initial implant and around a subsequent implant is that the coating is not continuous in the latter where the connector is secured to the case. This is of little moment because the Silastic coating does not function as an hermetic seal in the first place.

The overall assembly can be best appreciated by considering the exploded view of FIG. 3. A general description of the arrangement of parts will be described, followed by a more detailed consideration of the salient features of the invention.

Titanium case 10 is cup-shaped and can be made by machining a solid rod or by sheet metal forming. Two holes are drilled in the side of the cup for the coil insulating ceramic bushings 14. A platinum (in the preferred embodiment) tube 12 is attached to the bushings such that an hermetic seal is formed. The bushings are attached to the cup by using conventional ceramic-to-titanium brazing techniques (see 14a in FIG. 2), techniques which are well known to manufacturers of pacemakers.

Ceramic plate 32 (illustratively circular) contains multiple conducting feedthroughs 34. The manner of securing the feedthroughs in the ceramic plate and achieving an hermetic seal, as well as the detailed shape of the feedthroughs, will be described below. Titanium screw 42 is inserted through hole 32a of the ceramic plate, and the head of the screw is brazed to the underside of plate 32, around hole 32a, so that an hermetic seal is formed. At the time that the screw is attached to the ceramic plate containing the feedthroughs, the plate is brazed to titanium lid 44 around its circumference, as shown by the numeral 68 in FIG. 3A. It should be observed that screw 42 has a position which is generally central to the positions of the feedthroughs.

The electronic components are then assembled on lid 44 with electrical connections being made to all of the feedthroughs. The coil is wound within tube 12 as described above and the two ends are connected to the electronic circuits. Lid 44 is then attached to the wall of cup 10 with a circumferential weld using conventional TIG titanium welding techniques.

The electronic circuits inside the case may be mounted on a flexible printed circuit board which is soldered to the feedthroughs and the two ends of the coil. Alternatively, if the number of electronic components is small, they may be assembled inside the case using point-to-point wiring. For example, an integrated circuit chip carrier may be attached by glue to the end of the titanium screw, with wires being run between the feedthroughs and the connections on the chip carrier. Small components may be soldered in place onto the chip carrier, as may the end connections of the coil threaded through the tube.

The case thus completed is one part of the cochlear prosthesis package, the internal replaceable part. It should be noted that the unit is hermetically sealed. Although it might appear from the description thus far that the feedthroughs open the inside of the case to the outside, reference to FIG. 4, to be described in detail below, shows that the bottom of each feedthrough tube is closed (prior to lid 44 being welded to cup 10).

Figure 4:
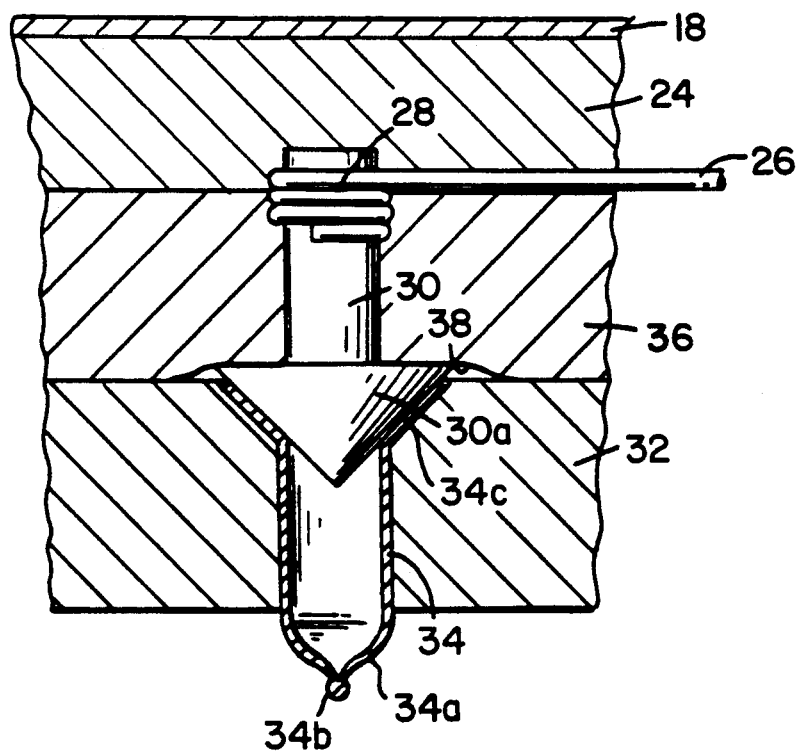
FIG. 4 is a detailed view showing the manner in which a connector contact is made with each of the feedthroughs.

The remaining elements in FIG. 3 constitute the connector for connecting the electrodes to the feedthroughs, the connector being permanently attached to the electrodes and ideally never requiring replacement. Silastic sheet 36 contains 22 preformed platinum parts 30 which mate with the feedthroughs on the ceramic plate 32. The preformed parts in FIG. 3 are shown as terminating in spheres, although in FIG. 4 their ends are shown as having a conical shape; these are only two of the possible shapes which may be used. FIG. 4, which depicts the construction of the elements associated with Silastic sheet 36, will be described in detail below. A wire 26 is connected to each connector element 30, and all of the wires are extended to electrode cable 16 (which does not form part of this invention). See, generally, "Development of Multichannel Electrodes For An Auditory Prosthesis", Report on Progress, Sep. 1, 1980 through Nov. 30, 1980, NIH Contract No. N01-NS-0-2337, by Merzenich et al.

Silastic sheet 24 is placed against the inside flat surface of a rigid titanium cover 18. Silastic sheet 36 is positioned against Silastic sheet 24. Actually, Silastic sheet 36 is molded inside cover 18. The cover is inverted and Silastic sheet 24 is placed in it. The 22 connector parts are then held in place while Silastic material is poured on top of sheet 24 in order that sheet 36 be formed to hold the connector parts. It should be noted that sheet 24 and cover 18 have a respective cut-out and hole 24a, 18a for allowing cable 16 to pass through the cover. Holes 36a, 24b and 18b allow screw 42 to pass through them during final assembly.

During the final assembly step, the connector is placed on top of ceramic plate 32, with each individual connector part in the connector being seated in a respective one of the feedthroughs as will be described in connection with FIG. 4. Screw 42 extends up through the connector and the two parts are held in compression against each other by tightening titanium nut 20 on the screw. The head on nut 20 sits in the depression which surrounds hole 18b in the cover.

FIG. 5A depicts the manner in which screw 42 is attached to the underside of ceramic plate 32. The screw is shaped so that it has an undercut 42a in its head. The brazing of the screw to the ceramic plate is shown at 50, and because of the undercut the brazing takes place on a thin ring around the edge of the screw head. The reason for insuring that the brazing takes place only along a thin ring is that were the brazing to be over the entire flat undersurface of the screw head, the brazed joint would be subject to strong shear forces during cooling after the brazing, and these shear forces would tend to break the bond. By insuring that the braze is only over a relatively small area, this effect is reduced. Undercut 42a, and the fact that the diameter of hole 32a is larger than the diameter of the screw, provide minimal contact between the screw and the ceramic feedthrough carrier.

An alternative embodiment for attaching the screw to the ceramic plate is shown in FIG. 5B. In this technique, another platinum tube 61 (of larger diameter and longer than the tubes used for the feedthroughs) is joined to the ceramic plate 60, in the same way as the platinum tubes for the connector contacts, that is, by reaction bonding. After attachment to the ceramic, the exposed end of the tube is flared (or this may be preformed prior to assembly) and a screw with a head of matching shape 62 is inserted into the platinum tube. The tube is then folded over the head of the screw and joined, e.g., by welding or brazing as shown by the numeral 63. This technique has the advantage that a metal-to-metal (i.e., platinum tube-to-screw) bond is required, and may thus be done in a variety of ways utilizing a variety of materials for the screw, e.g., titanium, platinum or biocompatible stainless steel. In addition, by appropriate choice of the shape of the screw head, all the rotational forces on the screw during tightening of the connector are not borne by the bond between the tube and the screw, but by the geometric arrangement of the screw head and tube. For example, if the screw head were hexagonal instead of circular, then the deformation of the platinum tube over the screw head would tend to strongly hold the screw in place. Thus the major function of the bond between the platinum tube and the screw is to provide an hermetic seal.

The feedthrough construction is illustrated in FIGS. 6A-6C. Green ceramic 32, formed to shape but not yet sintered, is sized so that following sintering and the resultant shrinking, the plate will fit in lid 44 (FIG. 3) as desired. Holes in the required positions for the feedthroughs are drilled in the green ceramic plate, and a further hole 32a is drilled to allow screw 42 (FIG. 3) to pass through it. Platinum tubes 34 are then placed in respective holes in the plate. The length of each tube, relative to the thickness of the plate, is shown in FIG. 6B. The tubes fit snugly in the holes in the plate, and they are placed so that a relatively large length protrudes from the upper surface of the plate (the surface which is shown as the undersurface in FIG. 3), and only a small length protrudes from the bottom. As seen most clearly in FIG. 6B, the thickness of the wall of each of tubes 34 is about one-tenth the outside diameter of the tube.

The green ceramic plate containing the platinum tubes in position is then placed on a flat surface within an oven and the oven is operated at the appropriate temperature and for the appropriate time necessary to sinter the ceramic plate. The sintering is no different from that of the prior art. As the ceramic sinters it shrinks, and thus shrinks around each of the platinum tubes. With the pressures involved due to the shrinkage, and the temperatures of sintering, a platinum reaction bond is formed between the ceramic and each platinum tube along its entire length in the ceramic around its circumference, to form an hermetic seal between the ceramic and the platinum tube. The process for forming so many hermetic seals in so tight a space is amazingly simple and cost-effective. The physics involved in the reaction bonding process is not completely understood. However, there is no question that the results are reproducible with every seal being hermetic. After sintering, the outer circumference of the plate may be ground to the correct dimensions, if necessary.

The general technique of reaction bonding metals to ceramics or glasses is known, and is used, for example, in the manufacture of high-temperature platinum thermocouples. However, prior art techniques require the application of external pressures under high temperature to achieve the bond. In the practice of the present invention, it is the forces associated with the shrinkage of the ceramic during sintering that achieves the bond. It is also known in the prior art to use ceramic which is initially sintered. The prior art techniques are described generally in Klomp, "Bonding of Metals to Ceramics and Glasses", Ceramic Bulletin, Volume 51, No. 9 (1972).

The ceramic plate is initially formed so that the bottom end of each feedthrough hole through the plate has a conical shape as shown by the numeral 32b in FIG. 6B. FIG. 6C depicts, in enlarged form, an individual platinum tube within the ceramic plate after the plate is fired and after subsequent processing. The bottom end of each tube is preferably formed to a concave shape, as shown by the numeral 34c in FIG. 6C, to provide a better contact area for the respective connector part. The bottom surface of the ceramic plate is then lapped to provide a high-quality "mirror" surface finish, for a reason to be described below. Finally, the upper end of each platinum tube (which is the lower end in FIG. 3) is closed off by using a standard welding technique, in order to complete the hermetic seal. The upper end is pinched, as shown by the numeral 34a in FIG. 6C, following which the tip is welded as shown by the numeral 34b.

Instead of forming the connector parts after firing, it is possible to use preformed platinum parts with closed ends. The region of the connector part which passes through the ceramic should be tubular. Reaction bonding has been found to take place when the connector part is a hollow tube in the region where the bonding is desired.

A similar technique is utilized for securing the ends of tube 12 within ceramic carrier bushings 14 (FIG. 3), since hermetic seals are also required for the tube ends. Ceramic bushings are made of green cermic, each having a central hole such that one end of hollow tube 12 fits snugly in the hole. (As in the case of ceramic plate 32, if there is a large degree of shrinking, the part being secured within a hole in a ceramic piece need not even fit snugly around the inserted tubular part.) The entire tube and the two bushings at its ends are then placed in an oven so that the ceramic bushings sinter. The bushings shrink and once again hermetic bonds are formed between each bushing and the platinum tube which it surrounds. A further advantage of this approach is that in the process the tube is annealed so that it may be easily and safely bent to any desired shape during implantation. After the bushings are thus attached to the ends of the tube, the bushings are attached to the titanium case 10 using any conventional brazing technique employed in fabricating pacemaker feedthroughs. During this process, care must be taken that none of the braze alloy be allowed to form an electrical connection between the metal case and the coil-enclosing tube. An important feature of the construction is that while the inside of the tube and the inside of the case are topologically continuous, they are not electrically connected so that the tube does not form a shorted turn which would otherwise absorb electromagnetic radiation to a significant degree.

An enlarged view of the manner in which a connector part makes contact with a feedthrough is shown in FIG. 4. Ceramic plate 32 is shown with a single feedthrough 34, the upper end of the feedthrough having a concavity 34c. At the bottom of the connector a platinum wire 30 terminates in a conical head 30a (although a spherical termination, as shown in FIG. 3, as well as other shapes, also suffice). An enlarged head is advantageous in that it contributes to better seating of the pin in the feedthrough, as well as providing a larger contact area. Pin 30 is held in molded Silastic sheet 36, this sheet bearing against Silastic sheet 24 which is adjacent to titanium cover 18. Pin 30 is connected to a wire 26, the wire in turn being extended through the electrode cable to a particular electrode. One end of wire 26 is resistance welded to pin 30, as shown by the numeral 28. Each of pins 30 is in reality nothing more than a short segment of wire, one of whose ends is formed into a desired shape. The wire has a diameter of 0.005 inches. The wire is too thick to be extended directly through the electrode cable, and wire 26 has a diameter of only 0.001 inches. It is for this reason that the two of them must be welded together within the connector; the wire which contacts the feedthrough is too thick for the electrode cable, and the wire in the electrode cable is too thin to establish sufficient contact with the feedthrough.

The upper surface of ceramic plate 32 is highly polished, as described above. Even though only a single screw is utilized for establishing the connection, due to the provision of Silastic sheet 24, Silastic sheet 36 is held against the ceramic plate with an even and consistent pressure. (It is metallic cover 18, of course, which distributes the screw force to the backing Silastic sheet 24.) Because of the uniform pressure throughout the interface between Silastic sheet 36 and ceramic plate 32 (resulting from the resiliency of the Silastic sheets), and because of the high polish on the surface of the latter, any fluid between the two surfaces is squeezed out into the empty space around head 30a of the connector part, the empty space being shown by the numeral 38 in FIG. 4. The fact that fluid may surround a connector part is of no moment; what would be a problem would be the existence of fluid between adjacent feedthroughs or connector parts and it is for this reason that fluid is excluded at the interface of the ceramic plate and Silastic sheet 36. The high polish of the ceramic plate prevents fluid from being trapped in microscopic depressions in the surface so that a very high inter-electrode resistance may be maintained.

It should be noted that the arrangement of connection points is such that the connector is self-locating, i.e., it can only be assembled in one way. Proper placement of the connector, with each of the 22 connector parts fitting in a respective feedthrough, can be sensed during assembly, and only when proper seating is achieved should nut 20 (FIG. 3) be tightened on screw 42.

Referring to FIGS. 1-3, it will be seen that tube 12 extends to one side of the circumference of the case. Because the case is outside the circumference of the coil, except for the short segment of the each turn which goes through the case between the ceramic bushings, the metal of the case does not significantly degrade the performance of the data and power link. It is because the two ends of the tube are not electricallly connected together that the tube does not act as a shorted turn which would otherwise absorb most of the radiated power. The tube simply acts as an open circuit turn, with potentials in the order of a volt being developed across its two ends.

Other orientations of the tube are possible. For example, the tube might be bent so that its plane is parallel with the plane of the case with the case contained within the tube. With such an orientation, transmission is still possible provided that the tube, with the coil inside, is between the case and the external transmitter/receiver. Of course, were the case to be interposed between the tube and the external device, the case would absorb practically all of the radiated power.

The use of a soft or ductile metal allows the tube to be bent to conform to the shape of the cavity into which the package is to be placed. The fact that there is little conductive metal within the coil (e.g., the wall of the tube) is advantageous in that any metal placed inside the coil absorbs power. Additional metal inside the coil comprises a short segment of the case wall between two ceramic bushings. Even this can be avoided if the case itself is made entirely of ceramic. The disadvantage of using ceramic material, however, is that a thicker wall thickness would be required, thus increasing the volume of the case.

It should also be appreciated that the shape of the tube need not be circular; any shape required by the implant and the anatomical site of implantation may be used. The diameter of the coil and its enclosing tube is not determined by the diameter of the case containing the electronic circuits, thus allowing flexibility in design and a reduction of the total volume of the implant. Another advantage of the use of the tube is that it may serve as a convenient anchoring point for the implant, either by using sutures or by including a fibrous mesh across the tube, should there be no other convenient way to anchor the implant.

Referring to FIG. 1, it will be seen that the unit is symmetrical around a vertical plane through the center. The advantage of this is that the package is not "handed", eliminating the need to make two different versions of the package for either side of the head.

The connector configuration satisfies all of the requirements for a cochlear prosthesis. The firm seating of the connected parts in the feedthroughs and the large contact areas insure that there is low electrical resistance in series with each electrode lead. Current leakage paths between connector points have high electrical resistance due to the usage of the Silastic/polished-ceramic interface. The connector may be disconnected and connected to another case a small number of times without any degradation in performance, even though reconnection in a fluid-surrounded body environment does not allow fluid ingress to be prevented.

Needless to say, one of the most important characteristics of the overall unit is that only well-proven biocompatible materials are used, including titanium, platinum, ceramic, and medical-grade Silastic.

Although the invention has been described with reference to a particular embodiment, it is to be understood that this embodiment is merely illustrative of the application of the principles of the invention. For example, the feedthrough pieces (which can be pre-formed) need not be circular in cross-section; an elliptical or even a non-uniform shape may be acceptable. Similarly, instead of platinum, other noble metals may be acceptable. Nor need the feedthroughs function in an electrical capacity. By utilizing tubes both of whose ends are not sealed, fail-safe communication can be had to a hostile environment, e.g., to sample chemical reactions such as in a blast furnace or in plastics manufacturing, to introduce reagents, or to perform a sensing function. The connector may be used for a cable-to-cable coupling rather than a cable-to-case coupling. In those cases where a telemetry capability is required, the package might be provided with only one tube bushing, solid or stranded wire being welded to the tube and functioning as an "aerial" with a free end. Thus it is to be understood that numerous modifications may be made in the illustrative embodiment of the invention and other arrangements may be devised without departing from the spirit and scope of the invention.

I claim:

1. A feedthrough assembly for a prosthetic implant, comprising: a carrier of a sintered ceramic material and having at least one hole therein, and at least one 2-ended hollow tubular feedthrough element of a platinum material extending axially through said at least one hole, said ceramic material having a sintering temperature of about 85-90% of the melting point of said platinum material and having the property of being solid both in its green state and its sintered state and of remaining solid but shrinking while being subjected to the sintering temperature during its transformation from its green state to its sintered state, said platinum material having the property of becoming partly plastic when subjected to a temperature of the magnitude of said sintering temperature, and said ceramic carrier and said at least one tubular feedthrough element being secured to each other by a reaction bond established circumferentially around said at least one tubular feedthrough element during the sintering of said ceramic carrier with said at least one tubular feedthrough element received in said at least one hole with a tight fit, whereby an hermetic seal is developed between said ceramic carrier and said at least one tubular feedthrough element without the application of a braze or other material to the juncture between said ceramic carrier and said at least one tubular feedthrough element.

2. A feedthrough assembly in accordance with claim 1, wherein one end of said at least one tubular feedthrough element is closed.

3. A feedthrough assembly in accordance with claim 1, wherein a face of said ceramic carrier is flat, only one end of said at least one tubular feedthrough element is sealed, the other end of said at least one tubular feedthrough element is conical in shape, said at least one hole in said ceramic carrier is conically flared at that end region of said at least one hole which intersects said face of said ceramic carrier, and said other end of said at least one tubular feedthrough element is seated in said conically flared end region of said at least one hole in said ceramic carrier such that said other end of said at least one tubular feedthrough element does not extend past said face of said ceramic carrier.

4. A feedthrough assembly in accordance with claim 3, wherein said face of said ceramic carrier has a high-quality mirror surface finish.

5. A feedthrough assembly for a prosthetic implant, comprising: a carrier of a sintered ceramic material and having a plurality of holes therein, and a like plurality of 2-ended hollow tubular feedthrough elements of a platinum material each extending axially through a respective one of said holes, said ceramic material having a sintering temperature of about 85-90% of the melting point of said platinum material and having the property of being solid both in its green state and its sintered state and of remaining solid but shrinking while being subjected to the sintering temperature during its transformation from its green state to its sintered state, said platinum material having the property of becoming partly plastic when subjected to a temperature of the magnitude of said sintering temperature, and said ceramic carrier and said tubular feedthrough elements being secured to each other by respective reaction bonds established circumferentially around each of said tubular feedthrough elements during the sintering of said ceramic carrier with said tubular feedthrough elements received in said holes each with a tight fit, whereby respective hermetic seals are developed between said ceramic carrier and said tubular feedthrough elements without the application of a braze or other material to the respective junctures between said ceramic carrier and said tubular feedthrough elements.

6. A feedthrough assembly in accordance with claim 5, wherein one end of each of said tubular feedthrough elements is closed.

7. A feedthrough assembly in accordance with claim 5, wherein a face of said ceramic carrier is flat, only one end of each of said tubular feedthrough elements is sealed, the other end of each of said tubular feedthrough elements is conical in shape, each of said holes in said ceramic carrier is conically flared at that end region of the respective hole which intersects said face of said ceramic carrier, and said other end of each of said tubular feedthrough elements is seated in said conically flared end region of its respective associated hole in said ceramic carrier such that said other ends of said tubular feedthrough elements do not extend past said face of said ceramic carrier.

8. A feedthrough assembly in accordance with claim 7, wherein said face of said ceramic carrier has a high-quality mirror surface finish.

* * * * *